(12) United States Patent
Smarrito-Menozzi et al.

(10) Patent No.: US 10,258,071 B2
(45) Date of Patent: Apr. 16, 2019

(54) SUGAR-DIPEPTIDE CONJUGATES

(71) Applicant: NESTEC S.A., Vevey (CH)

(72) Inventors: Candice Marie Smarrito-Menozzi, Belmont-sur-lausanne (CH); Florian Viton, Lausanne (CH); Thomas Hofmann, Neufahrn (DE); Maximillian Kranz, Freising (DE)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 15/558,403

(22) PCT Filed: Mar. 8, 2016

(86) PCT No.: PCT/EP2016/054877
§ 371 (c)(1),
(2) Date: Sep. 14, 2017

(87) PCT Pub. No.: WO2016/146432
PCT Pub. Date: Sep. 22, 2016

(65) Prior Publication Data
US 2018/0055078 A1 Mar. 1, 2018

(30) Foreign Application Priority Data
Mar. 19, 2015 (EP) .................................. 15159896

(51) Int. Cl.
*A23L 27/00* (2016.01)
*A23L 27/21* (2016.01)
*A23L 23/00* (2016.01)
*C07K 9/00* (2006.01)
*C07K 1/107* (2006.01)
*C07K 5/062* (2006.01)

(52) U.S. Cl.
CPC ............. *A23L 27/215* (2016.08); *A23L 23/00* (2016.08); *A23L 27/00* (2016.08); *C07K 1/1077* (2013.01); *C07K 5/06026* (2013.01); *C07K 9/001* (2013.01); *A23V 2002/00* (2013.01)

(58) Field of Classification Search
None
See application file for complete search history.

(56) References Cited

U.S. PATENT DOCUMENTS

2007/0037243 A1  2/2007  Hirokawa et al.

FOREIGN PATENT DOCUMENTS

EP   2119372   11/2009

OTHER PUBLICATIONS

Abbott et al. "Novel solvent properties of choline chloride/urea mixtures" Chem. Commun., 2003, pp. 70-71.

*Primary Examiner* — Elizabeth Gwartney
(74) *Attorney, Agent, or Firm* — K&L Gates LLP

(57) ABSTRACT

The present invention relates to a method for making a sugar-dipeptide conjugate. In particular the invention concerns a method for making a sugar-dipeptide conjugate comprising forming a liquid eutectic mixture of at least two compounds solid at 25° C. and water, and heating the liquid eutectic mixture; wherein the liquid eutectic mixture comprises a dipeptide and a reducing sugar. A further aspect of the invention is a method for preparing a food product.

12 Claims, 3 Drawing Sheets

SUGAR-DIPEPTIDE CONJUGATES

CROSS REFERENCE TO RELATED APPLICATIONS

The present application is a National Stage of International Application No. PCT/EP2016/054877, filed on Mar. 8, 2016, which claims priority to European Patent Application No. 15159896.8, filed on Mar. 19, 2015, the entire contents of which are being incorporated herein by reference.

FIELD OF THE INVENTION

The present invention relates to a method for making a sugar-dipeptide conjugate. In particular the invention concerns a method for making a sugar-dipeptide conjugate comprising forming a liquid eutectic mixture of at least two compounds solid at 25° C. and water, and heating the liquid eutectic mixture; wherein the liquid eutectic mixture comprises a dipeptide and a reducing sugar. A further aspect of the invention is a method for preparing a food product.

BACKGROUND OF THE INVENTION

Many foods that are consumed today are rich in umami taste. Umami represents the taste of the amino acid L-glutamate and 5'-ribonucleotides such as guanosine 5'-monophosphate (GMP) and 5'-inosine monophosphate (IMP) and is sometimes also called the fifth taste. The word umami derives from the Japanese for delicious and the umami taste can be described as "savoury", "brothy" or "meaty" taste. The sensation of umami is due to the activation of taste receptor cells assembled into taste buds, distributed across different papillae of the tongue and the palate epithelium (Chandrashekar et al., 2006, Nature, 444, 288-294). Its effect is to balance taste and round out the overall flavor of a dish. Furthermore, umami enhances the palatability of a wide variety of food products. Naturally occurring glutamate can be found for example in many meat and vegetable food preparations (Ghirri et al., 2012, International Journal of Food Sciences and Nutrition, 63(7), 872-881.).

Umami or savoury, meaty taste of a food product can be further achieved and/or enhanced by adding separately monosodium glutamate (MSG) and/or the ribonucleotides GMP and IMP into those culinary recipes. Many taste enhancers comprising such MSG and/or ribonucleotides have been developed by the food industry and are available world-wide in the trade. A wide variety of ready-to-use taste enhancers are therefore available for various different culinary applications and in various different forms such as pastes, powders, liquids, compressed cubes or granules.

The addition of those culinary additives helps to provide deliciousness and enhanced taste appealing properties to food products to which they were added. Indeed, all around the world, deliciousness and appealing taste is perceived as one of the key attributes of a high quality meal. However, in many parts of the world, the addition of MSG and/or ribonucleotides has received bad press and is more and more negatively perceived by consumers. Although MSG and those ribonucleotides are naturally occurring in many food products, such as in tomatoes and meat products, and have been proven to be safe by several organizations including the World Health Organisation (WHO) and the European Food Safety Authority (EFSA), a publication in the New England Journal of Medicine (Kwok, R H M, 1968 New England Journal of Medicine, 278 (14), 796) sparked speculation among consumers about detrimental effects of MSG and ribonucleotides leading many consumers to reject products containing large amounts of such added compounds. There is therefore a strong need for industrial solutions allowing reducing the use of added MSG and ribonucleotides to food or taste enhancing products, without however compromising on umami taste and still ensuring savoury superiority of such culinary products.

For example, in a recent scientific publication from A. Dunkel and T. Hofmann (Dunkel and Hofmann, 2009, J. Agric. Food Chem. 2009, 57, 9867-9877), sensory-directed fractionation of a freshly prepared double-boiled chicken soup led to the identification of the β-alanyl dipeptides, L-anserine, L-carnosine and β-alanylglycine as contributors to the thick-sour and white-meaty orosensation. Quantitative analysis, followed by taste recombination and omission experiments, revealed for the first time that, when present together with L-glutamic acid and sodium and/or potassium ions, sub-threshold concentrations of these three β-alanyl peptides enhance the typical thick-sour orosensation and white-meaty character known for poultry meat. This is a first step in finding new compounds which are able to impart flavour richness and enhance the umami taste effect of MSG, and thereby allowing a reduced use of MSG.

In our co-pending applications EP15153278.5 and EP 15153288.4 we describe how sugar conjugates of dipeptides have a much stronger flavour enhancing effect than their corresponding aglycones. In fact, these sugar conjugates enhance umami perception and induce a thick-sour and white meaty orosensation of a culinary recipe at much lower threshold levels than their corresponding aglycones. Therefore, the sugar-dipeptide conjugates (such as sugar-β-alanyl dipeptide molecules) are more potent flavour and umami taste enhancers than their corresponding aglycones (such as β-alanyl dipeptides). They allow further reducing the amounts and uses of MSG and/or ribonucleotides in culinary food products without compromising flavour richness and/or reducing the typical and well desired umami taste of said products. They also allow generating umami savoury food concentrates which have much less or no MSG and/or ribonucleotides and still provide a strong and typical umami taste if applied to a food product. It even allows generating such umami savoury food concentrates which are much stronger and more concentrated in providing an umami taste to a food product upon application.

Sugar-dipeptide conjugates may be generated in-situ during thermal processing of food raw materials, for example the formation of sugar-β-alanyl dipeptide molecules by condensation of glucose with β-alanyl-dipeptides such as carnosine and anserine. However, the generation of sugar-dipeptide conjugates in such systems are difficult to control and provide low yields. Sugar-dipeptide conjugates may be synthesised, for example in organic solvents, but these solvents are often not suitable for incorporation in food and so the sugar-dipeptide conjugates must undergo expensive purification steps.

There is a need to be able to generate sugar-dipeptide conjugates in high yields and under reproducible conditions. In particular there is a need to be able to generate sugar-dipeptide conjugates using materials and processes which are suitable for the safe production of food ingredients. Ideally all the materials of the reaction mixture are suitable for use in food so the mixture can be incorporated directly. It would be advantageous if the number of different materials in the reaction mixture were minimized, especially materials which are poorly perceived by consumers of food products.

The object of the present invention is to improve the state of the art and to provide an alternative or improved solution to the prior art to overcome at least some of the inconveniences described above. Particularly, the object of the present invention is to provide an alternative or improved solution for making sugar-dipeptide conjugates. The object of the present invention is achieved by the subject matter of the independent claims. The dependent claims further develop the idea of the present invention. Any reference to prior art documents in this specification is not to be considered an admission that such prior art is widely known or forms part of the common general knowledge in the field. As used in this specification, the words "comprises", "comprising", and similar words, are not to be interpreted in an exclusive or exhaustive sense. In other words, they are intended to mean "including, but not limited to".

SUMMARY OF THE INVENTION

Accordingly, the present invention provides in a first aspect a method for making for making a sugar-dipeptide conjugate, the method comprising forming a liquid eutectic mixture of at least two compounds solid at 25° C. and water, the water being present in an amount insufficient to dissolve all the compounds solid at 25° C. individually, or in an amount such that all the compounds solid at 25° C. are simultaneously saturated at 25° C.; and heating the liquid eutectic mixture at a temperature greater than 30° C. for at least 10 minutes; wherein the liquid eutectic mixture comprises a dipeptide and a reducing sugar. In a second aspect, the invention relates to a method for preparing a food product comprising generating a sugar-dipeptide conjugate according to the method of the invention; providing food components and combining the sugar-dipeptide conjugate and food components to form a food product.

The inventors surprisingly found that by reacting a dipeptide and a reducing sugar in a low moisture-content liquid eutectic mixture they were able to achieve higher yields than in a methanol/glycerol system. It is not desirable to use methanol as a solvent for processing a food ingredient as it is toxic. Reacting the dipeptide and reducing sugar in the low moisture-content liquid eutectic mixture generated much higher yields than the same reaction in aqueous solution and could be performed at lower temperatures than for the aqueous solution, without the addition of salts and buffers.

DETAILED DESCRIPTION OF THE INVENTION

Figure 1:
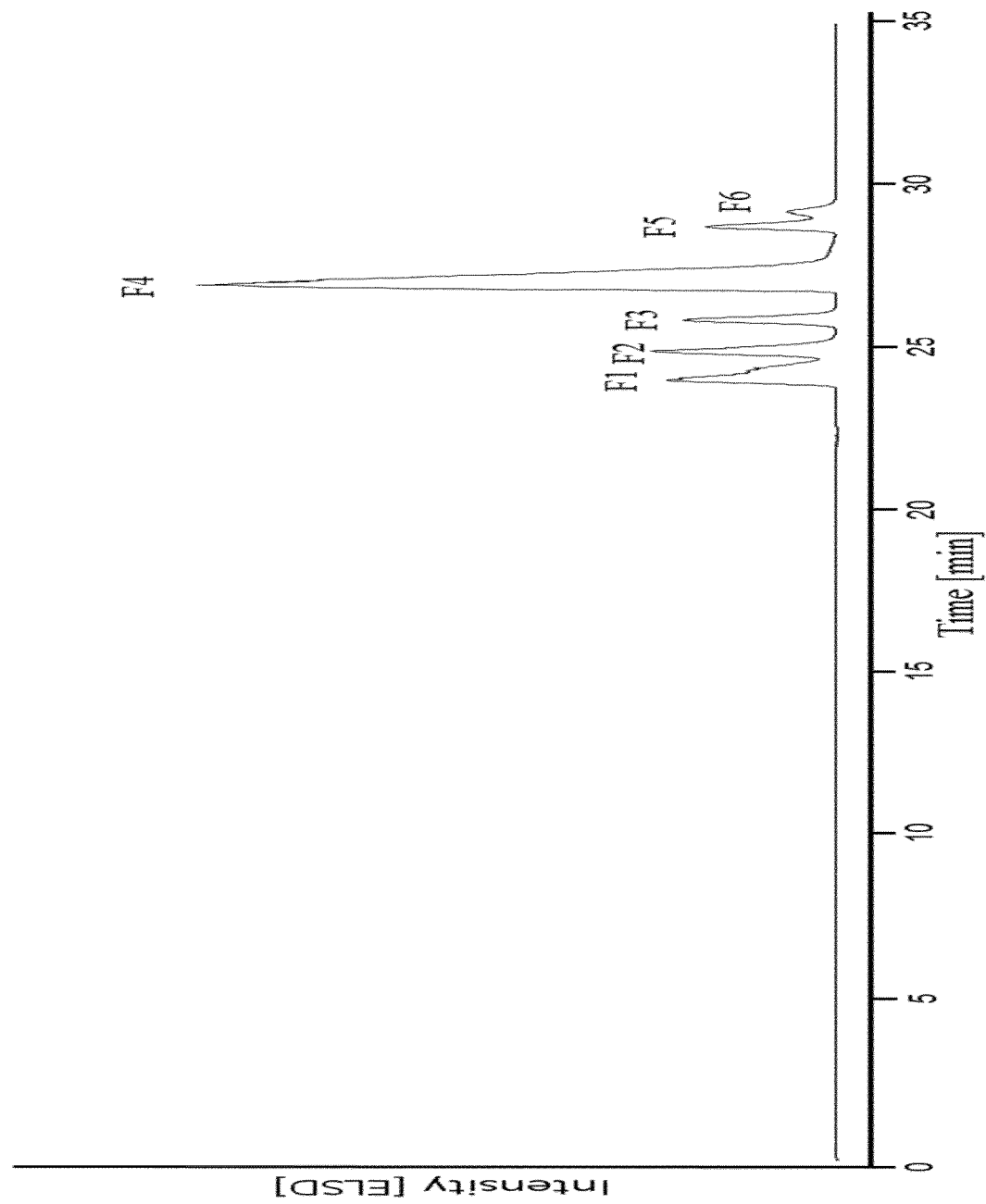
FIG. 1 is an HPLC-UV chromatogram of a thermally treated carnosine with glucose.

Consequently the present invention relates in part to a method for making a sugar-dipeptide conjugate, the method comprising forming a liquid eutectic mixture of at least two compounds solid at 25° C. and water, the water being present in an amount insufficient to dissolve all the compounds solid at 25° C. individually, or in an amount such that all the compounds solid at 25° C. are simultaneously saturated at 25° C.; and heating the liquid eutectic mixture at a temperature greater than 30° C. (for example greater than 40° C., for example greater than 50° C.) for at least 10 minutes (for example at least 30 minutes, for example at least 1 hour); wherein the liquid eutectic mixture comprises a dipeptide and a reducing sugar. The at least two compounds solid at 25° C. may be a dipeptide and a reducing sugar.

The liquid eutectic mixture may comprise glucose and sucrose. For example a liquid eutectic mixture may be formed by dissolving 5.0 g glucose and 9.5 g sucrose in 30 mL water and then concentrating the resulting solution to give a liquid eutectic mixture with 1.6 g water. Both glucose and sucrose are solid at 25° C. From literature values only about 3.3 g sucrose would dissolve in 1.6 g water at 25° C., so the solubility of sucrose in water is not high enough for 9.5 g sucrose to dissolve in 1.6 g water. Similarly, only about 1.7 g glucose would dissolve in 1.6 g water at 25° C., so the solubility of glucose in water is not high enough for 5.0 g glucose to dissolve in 1.6 g water. However, with glucose and sucrose together, the mixture can exist as a homogeneous liquid, a liquid eutectic mixture. The melting point of this liquid eutectic mixture is much lower than the melting point of the compounds which form the eutectic mixture (this is sometimes referred to as a deep eutectic solvent or a deep eutectic system (DES)). The liquid eutectic mixture formed from the at least two compounds solid at 25° C. and water in the method of the invention may have a melting point at least 20° C. lower than the lowest individual melting point of the compounds which form the liquid eutectic mixture, for example at least 30° C. lower than the lowest individual melting point of the compounds which form the liquid eutectic mixture.

Sugar dipeptide conjugates are molecules which may be formed by a condensation reaction between a sugar and a dipeptide. In the context of the present invention the term dipeptide refers to two amino acids joined by a single peptide bond. Examples of sugar dipeptide conjugates are 1-deoxy-D-fructosyl-N-β-alanyl-L-histidine, 1-deoxy-D-fructosyl-N-β-alanyl-N-methyl-L-histidine, 1-deoxy-D-fructosyl-N-β-alanyl-L-glycine, xylulosyl-N-β-alanyl-L-histidine, xylulosyl-N-β-alanyl-N-methyl-L-histidine and xylulosyl-N-β-alanyl-L-glycine.

Reducing sugars are sugars that either have an aldehyde group or are capable of forming one in solution through isomerism. The aldehyde functional group allows the sugar to act as a reducing agent. The reducing sugar in the method of the invention may be selected from the group consisting of xylose, fructose and glucose. For example the reducing sugar may be glucose. For example the reducing sugar may be xylose. The dipeptide in the method of the invention may be a β-alanyl dipeptide, for example the dipeptide may be selected from the group consisting of carnosine, anserine and β-alanylglycine. These dipeptides provide potent flavour and umami taste enhancers when formed into sugar conjugates. For example the reducing sugar may be glucose and the dipeptide may be carnosine. For example the reducing sugar may be glucose and dipeptide may be anserine. For example the reducing sugar may be glucose and the dipeptide may be β-alanylglycine. For example the reducing sugar may be xylose and the dipeptide may be carnosine. For example the reducing sugar may be xylose and dipeptide may be anserine. For example the reducing sugar may be xylose and the dipeptide may be β-alanylglycine.

The sugar-dipeptide conjugate of the method of the invention may be a food ingredient. It is advantageous that the method of the invention may be performed with all materials being edible. The term "edible" refers to substances which can be eaten safely. Whilst not being limited to substances permitted for consumption in any particular jurisdiction, edible materials used in the method of the invention may for example comprise materials approved for human consumption by the U.S. Food and Drug Administration.

It is advantageous that the method of the invention may provide high product yields without the need to add inorganic salts, for example to control pH. Such inorganic salts would be carried through into the mixture generated by the method. For food materials it can be beneficial to limit the number of ingredients, for example to reduce the number of ingredients which appear on the food product's ingredient list. The liquid eutectic mixture in the method of the invention may contain less than 500 ppm inorganic salts, for example the liquid eutectic mixture may be free from inorganic salts.

Liquid eutectic mixtures may be formed in a number of ways, for example the solid compounds may be dissolved directly in an amount of water insufficient to dissolve all the compounds individually. This generally works well for the higher quantities of water, the dissolution being aided by stirring. The liquid eutectic mixture may also be formed by combining the solid compounds and storing them in a humid atmosphere until a liquid mixture is formed, although this may take too long for an industrial application. For liquid eutectic mixtures having low amounts of water it may be easier to first dissolve the solid compounds in an excess of water and then remove some of the water by evaporation to leave a liquid eutectic mixture. For example, the liquid eutectic mixture in the method of the invention may be formed by first dissolving the at least two compounds solid at 25° C. in an amount of water sufficient to dissolve all the compounds solid at 25° C. individually, and then concentrating the resulting solution until the water is present in an amount insufficient to dissolve all the compounds solid at 25° C. individually.

The dipeptide and the reducing sugar in the method of the invention do not necessarily need to be present in exact stoichiometric quantities. For example the dipeptide and the reducing sugar may be present in a molar ratio between 1:0.02 and 1:50, for example between 1:0.5 and 1:45.

The liquid eutectic mixture in the method of the invention may comprise glucose, β-alanyldipeptide and water. For example, to form 1-deoxy-D-fructosyl-N-β-alanyl-L-histidine, the liquid eutectic mixture in the method of the invention may comprise glucose, carnosine and water, for further example the liquid eutectic mixture in the method of the invention may consist of glucose, carnosine and water. The liquid eutectic mixture in the method of the invention may comprise a polyol such as a sugar, solid at 25° C. The liquid eutectic mixture in the method of the invention may comprise a polyol solid at 25° C., glucose, β-alanyldipeptide and water. The liquid eutectic mixture in the method of the invention may comprise glucose, sucrose, β-alanyldipeptide and water. For example, to form 1-deoxy-D-fructosyl-N-β-alanyl-L-histidine, the liquid eutectic mixture in the method of the invention may comprise glucose, sucrose, carnosine and water, for further example the liquid eutectic mixture in the method of the invention may consist of glucose, sucrose, carnosine and water.

The liquid eutectic mixture in the method of the invention may comprises glucose, and the molar ratio of glucose to water in the liquid eutectic mixture may be between 1:9.5 and 1:2.5, for example between 1:5 and 1:3. These ratios provide particularly good results.

The sugar-dipeptide conjugate formed by the method of the invention may be used to enhance the flavour and/or the umami taste of a food product. Such a food product may be a ready-to-eat food product. It may also be a flavour concentrate used for seasoning a still further other food product. In a further aspect, the invention provides a method for preparing a food product comprising making a sugar-dipeptide conjugate according to the method of the invention; providing food components and combining the sugar-dipeptide conjugate and food components to form a food product. For example the food product prepared by the method of the invention may be a culinary seasoning; a cooking aid (for example a concentrated bouillon); a sauce, for example a sauce concentrate; a soup, for example a soup concentrate or a pet-food product, for example a wet pet-food product or a dry pet-food product.

Those skilled in the art will understand that they can freely combine all features of the present invention disclosed herein. In particular, features described for different embodiments of the present invention may be combined. Where known equivalents exist to specific features, such equivalents are incorporated as if specifically referred to in this specification. Further advantages and features of the present invention are apparent from the figures and non-limiting examples.

EXAMPLES

Example 1 (Comparative): Synthesis of 1-deoxy-D-fructosyl-N-β-alanyl-L-histidine from Glucose and Carnosine (β-alanyl-L-histidine) in Methanol/Glycerol Chemicals:
Sodium bisulphite and glycerol were purchased from Sigma, glucose from SDfine Chemicals, carnosine from ChemImprex, methanol and acetic acid from Merck. All commercially available reagents were used as received from their respective suppliers.

Analytical thin layer chromatography (TLC) was carried out on RP-18 F254s (Merck) plates. The TLC plates were visualized by shortwave UV light, Ninhydrin stain.

$^1$H NMR (360.13 MHz) and $^{13}$C NMR (90.56 MHz) spectra were recorder on a Bruker DPX-360 spectrometer equipped with a broadband multinuclear z-gradient probehead. The chemical shifts (in ppm) were expressed with respect to an internal reference (TMS or TSP). Multiplicities are reported as follows: s=singlet, d=doublet, t=triplet, q=quadruplet, m=multiplet, bs=broad singlet.

D-Glucose (23 g, 127.37 mmol, 2.8 eq.) and sodium bisulfite (1.6 g, 12.389 mmol, 0.28 eq.) were suspended in methanol (38 mL) and glycerol (19 mL). After stirring for 30 min at 100° C., carnosine (10 g, 44.22 mmol, 1.0 eq.) and acetic acid (5.1 mL) were added and the resulting mixture was heated for 3.5 hours at 100° C. Reaction mass was then cooled down and diluted with 38 mL water. The reaction mixture was purified using a column packed in Amberlite IRN-77 ion exchange resin (100 g). NH$_3$ 0-0.4% was used as gradient in water for elution. Finally, 6.8 g 1-deoxy-D-fructosyl-N-β-alanyl-L-histidine were isolated; Rf (n-Butanol:Acetic Acid:Water, 3:2:2): 0.21; MS (M$^+$): m/z 388.16; $^1$H NMR (Deuterium Oxide) δ 2.77 [m, 2H], 3.13 [dd, J=15.4, 8.2 Hz, 1H], 3.21-3.27 [m, 1H], 3.28-3.32 [m, 2H], 3.33-3.44 [m, 2H], 3.63-3.75 [m, 1H], 3.76-3.85 [m, 2H], 3.87-3.91 [m, 1H], 3.99-4.03 [m, 2H], 4.53 [dd, J=8.2, 5.2

Hz, 1H], 7.28 [d, J=1.0 Hz, 1H], 8.61 [d, J=1.4 Hz, 1H]; $^{13}$C NMR (Deuterium Oxide) δ 26.98, 30.26, 44.28, 53.01, 53.92, 63.91, 68.80, 69.20, 69.76, 95.21, 116.65, 129.49, 133.15, 171.60, 176.13.

The formation yield of 1-deoxy-D-fructosyl-N-β-alanyl-L-histidine was 39.62%. Formation yield refers to the number of moles of conjugates formed, expressed as a percentage of the theoretical maximum number of moles which could be produced by that quantity of starting materials (based on the stoichiometry of the reaction).

Example 2 (Comparative): Preparation of 1-deoxy-D-fructosyl-N-β-alanyl-L-histidine from Glucose and Carnosine in Buffer at Different pH A mixture of carnosine (226 mg, 1 mmol, 1 eq.) and glucose (360 mg, 2 mmol, 1 eq.) in 20 mL Na$_2$HPO$_4$ buffer (0.5 mol/L, pH 3.0/5.0/7.0) was heated in a closed vessel at 80° C. for 3 h. The solvent was then evaporated under reduced pressure and the resulting precipitate was freeze-dried. Aliquots of the freeze-dried powder were dissolved in water upon ultrasonification for 10 min and filtrated (0.45 μm). The solutions were then fractionated by a semi-preparative hydrophilic interaction liquid chromatography (HILIC-HPLC) using a 300×21.5 mm i.d., 10 μm, TSKgel Amide-80 column (Tosoh Bioscience, Stuttgart, Germany) equipped with a 75×21.5 i.d., 10 μm, guard column (Tosoh Bioscience, Stuttgart, Germany). Monitoring the effluent with an ELSD detector (Evaporative Light Scattering Detector) and adjusting the flow rate to 8 mL/min, a gradient consisting of aqueous formic acid (1% in water, solvent A) and acetonitrile (solvent B) was used. Starting with a mixture of 75% B and 25% A for 10 min, the gradient was reduced successively to 0% B and 80% A within another 10 min. After holding these conditions for 5 min, the gradient was increased to 75% B and 25% A within 8 min. The purification led to 6 fractions as shown in the FIG. 1.

The molecule corresponding to fraction F5 was identified as carnosine while the molecule F6 was identified as 1-deoxy-D-fructosyl-N-β-alanyl-L-histidine (based on LC-MS and NMR data).

Quantification of 1-deoxy-D-fructosyl-N-β-alanyl-L-histidine was done by stable isotopic dilution analysis using a HPLC-MS equipped with TSKgel-Amide 80 column (3 μm, 2 mm×150 mm from Tosoh Bioscience, Stuttgart, Germany) and the guard column TSKgel-Amide 80 (3 μm, 2 mm×10 mm from Tosoh Bioscience, Stuttgart, Germany). The eluent A was a mixture of acetonitrile with 1.0% formic acid and the eluent B was water with 1.0% formic acid. The injection volume was 3 μL. The flow rate was 0.2 mL/min. The solvent gradient started at 95% A from 0 to 5 min then 95-5% A from 5 to 15 min, 5% A for 10 min, 5-95% from 27 to 30 min. Table 1 summarizes MS conditions.

TABLE 1

Mass transitions

| Substance | MW [Da] | Q1 → Q3 [m/z] | DP[a] | CE[b] | CXP[c] |
|---|---|---|---|---|---|
| 1-Deoxy-D-fructosyl-N-β-alanyl-L-histidine | 388 | 389 → 305 | 71 | 25 | 4 |

[a]Declustering Potential;
[b]Collision Energy;
[c]Cell Exit Potential

Figure 2:
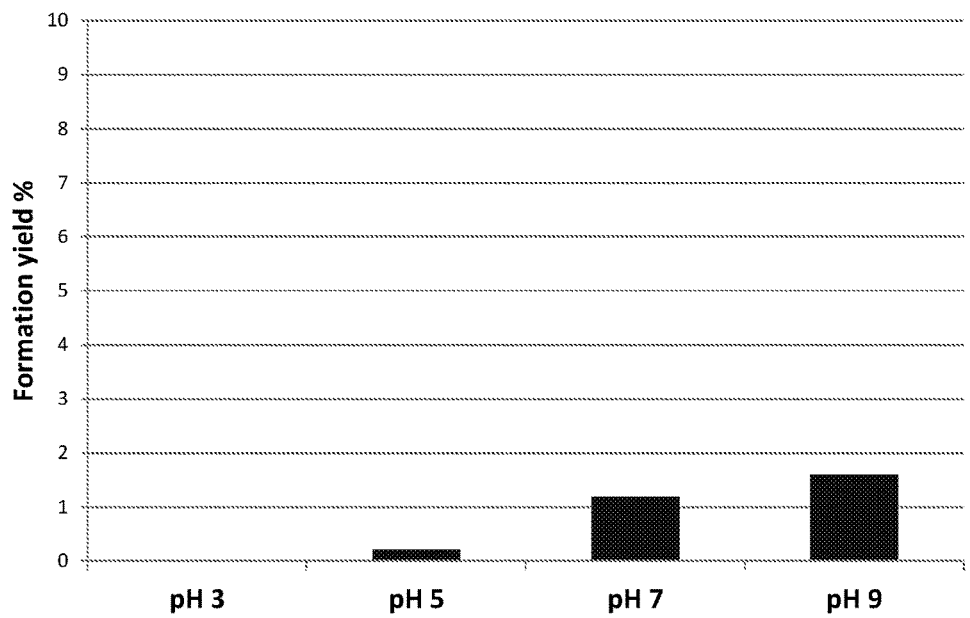
FIG. 2 shows the formation yield of 1-deoxy-D-fructosyl-N-β-alanyl-L-histidine at different pH values

The influence of pH on the yield of 1-deoxy-D-fructosyl-N-β-alanyl-L-histidine is shown in FIG. 2. The highest yield was 1.6%, obtained at pH 9.

Example 3 (Comparative): Preparation of 1-deoxy-D-fructosyl-N-β-alanyl-L-histidine from Glucose and Carnosine in Buffer at Different Temperatures A mixture of carnosine (226 mg, 1 mmol, 1 eq.) and glucose (360 mg, 2 mmol, 1 eq.) in 20 mL Na$_2$HPO$_4$ buffer (0.5 mol/L, pH 7.0) was heated in a closed vessel at 40/60/80/100° C. for 3 h. The resulting mixtures were analyzed as described in Example 2.

Figure 3:
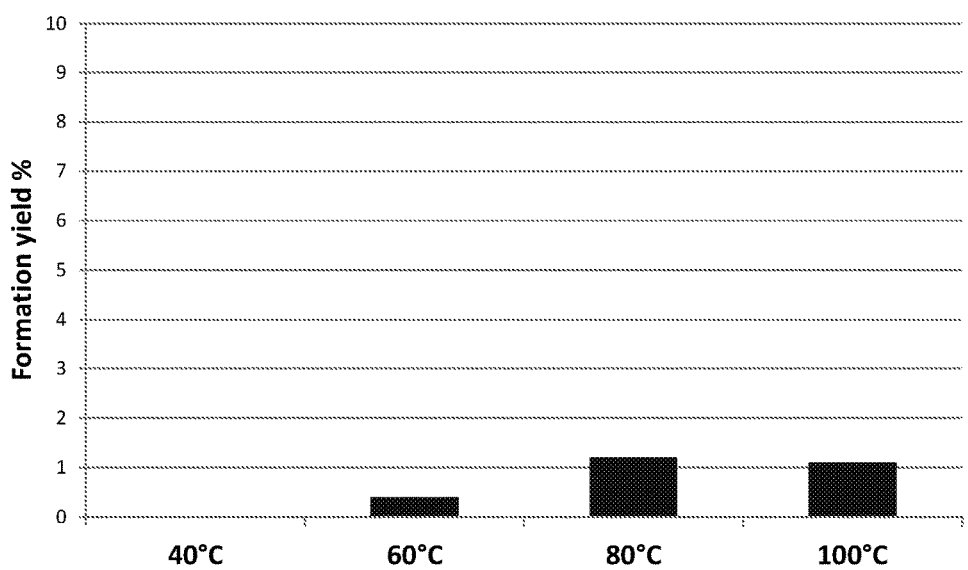
FIG. 3 shows the formation yield of 1-deoxy-D-fructosyl-N-β-alanyl-L-histidine at various heating temperatures

Influence of the heating temperature on the yield of 1-deoxy-D-fructosyl-N-β-alanyl-L-histidine is shown in FIG. 3. The highest yield was 1.2%, obtained at 80° C.

Example 4 (Comparative): Preparation of 1-deoxy-D-fructosyl-N-β-alanyl-L-histidine from Glucose and Carnosine (8-alanyl-L-histidine) in Buffer at Different Heating Times A mixture of carnosine (226 mg, 1 mmol, 1 eq.) and glucose (360 mg, 2 mmol, 1 eq.) in 20 mL Na$_2$HPO$_4$ buffer (0.5 mol/L, pH 7.0) was heated in a closed vessel at 80° C. for 0.5 to 3 h. The resulting mixtures were analyzed as described in Example 2.

Figure 4:
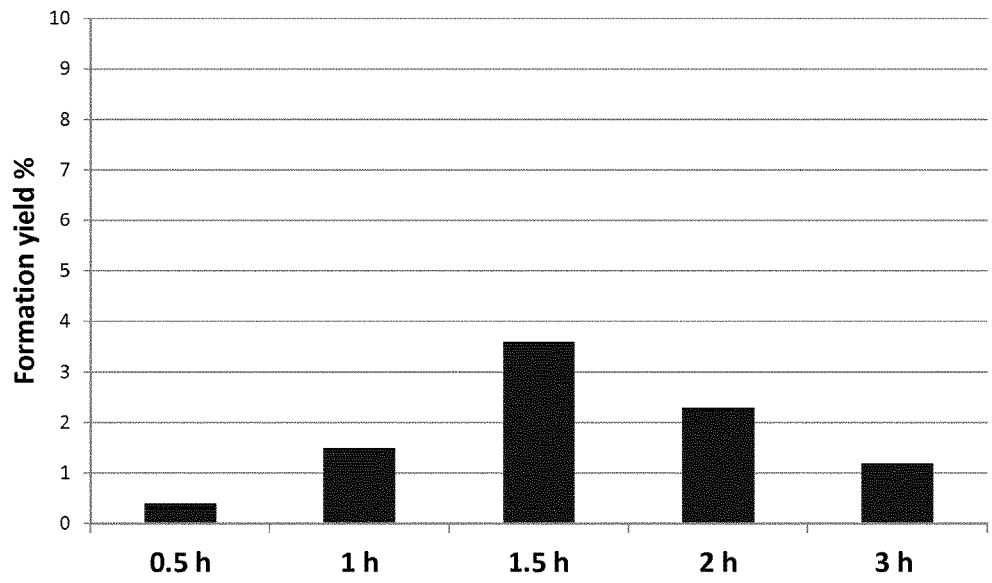
FIG. 4 shows the formation yield of 1-deoxy-D-fructosyl-N-β-alanyl-L-histidine at different heating times

Influence of the heating time on the yield of 1-deoxy-D-fructosyl-N-β-alanyl-L-histidine is shown in FIG. 4. The highest yield was 3.6%, obtained after 1.5 hours.

Example 5: Preparation of 1-deoxy-D-fructosyl-N-β-alanyl-L-histidine from Glucose and Carnosine (8-alanyl-L-histidine) in a Liquid Eutectic Mixture [Glucose/Sucrose] at Different Heating Times Preparation of liquid eutectic mixture from glucose and sucrose: 5.0 g glucose (28 mmol) and 9.5 g sucrose (28 mmol) were dissolved in 30 mL water. The resulting solution was then concentrated under reduced pressure at 50° C. to give a liquid eutectic mixture consisting of glucose and sucrose at a molar ratio of 50/50 with 9.93% H$_2$O. Sniffing the liquid eutectic mixture confirmed that there had been no change in aroma during the process of forming the liquid eutectic mixture.

150 mg carnosine (0.664 mmol) was added to 14.50 g of liquid eutectic mixture of glucose/sucrose (molar ratio 50/50, 9.93% H$_2$O) and the resulting mixture was heated for 1, 2 or 6 hours at 60° C. Quantification of 1-Deoxy-D-fructosyl-N-β-alanyl-L-histidine was performed as described in Example 2.

Figure 5:
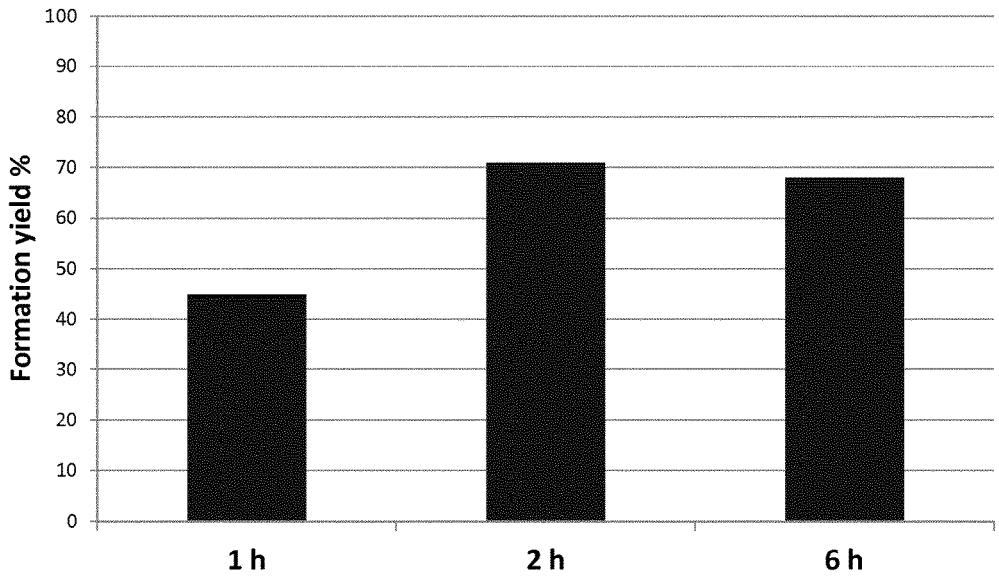
FIG. 5 shows the formation yield of 1-deoxy-D-fructosyl-N-β-alanyl-L-histidine in a liquid eutectic mixture

Influence of the heating time on the yield of 1-deoxy-D-fructosyl-N-β-alanyl-L-histidine is shown in FIG. 5. A yield of 71% was obtained after a heating time of 2 hours. It can be seen that reacting glucose and carnosine in a liquid eutectic mixture results in a higher yield of 1-deoxy-D-fructosyl-N-β-alanyl-L-histidine than when glucose and carnosine are reacted in a methanol/glycerol solvent (Example 1). The reaction in a liquid eutectic mixture results in yields of 1-deoxy-D-fructosyl-N-β-alanyl-L-histidine more than an order of magnitude greater than when glucose and carnosine are reacted in aqueous systems (Examples 2, 3 and 4).

Example 6: Preparation of 1-deoxy-D-fructosyl-N-β-alanyl-L-histidine in a Liquid Eutectic Mixture [Glucose/Carnosine]

Preparation of a liquid eutectic mixture from glucose and carnosine: 0.3982 g glucose (2.2 mmol) and 0.5000 g carnosine (2.2 mmol) were dissolved in 30 mL water. The resulting solution was then concentrated under reduced pressure at 50° C. to give a liquid eutectic mixture consisting of glucose and carnosine at a molar ratio of 50/50 with 6.40% $H_2O$. Sniffing the liquid eutectic mixture confirmed that there had been no change in aroma during the process of forming the liquid eutectic mixture.

0.9 g of DES glucose/carnosine (molar ratio 50/50, 6.40% $H_2O$) was heated for 2 hours at 60° C. to give the 1-Deoxy-D-fructosyl-N-β-alanyl-L-histidine in a yield of 59.7±2.3%. (Quantification was performed as described in Example 2). This shows that reacting glucose and carnosine as a liquid eutectic mixture results in a higher yield of 1-deoxy-D-fructosyl-N-β-alanyl-L-histidine than when glucose and carnosine are reacted in a methanol/glycerol solvent (Example 1). The reaction of glucose and carnosine as a liquid eutectic mixture results in a yield of 1-deoxy-D-fructosyl-N-β-alanyl-L-histidine more than an order of magnitude greater than when glucose and carnosine are reacted in aqueous systems (Examples 2, 3 and 4).

The invention claimed is:

1. A method for making a sugar-depeptide conjugate comprising: forming a liquid eutectic mixture of at least two compounds solid at 25° C. and water, the water being present in an amount insufficient to dissolve all of the compounds solid at 25° C. individually, or in an amount such that all the compounds solid at 25° C. are simultaneously saturated at 25° C.; and heating the liquid eutectic mixture at a temperature greater than 30° C. for at least 10 minutes; wherein the liquid eutectic mixture comprises a dipeptide and a reducing sugar.

2. The method according to claim 1 wherein the reducing sugar is selected from the group consisting of xylose, fructose and glucose.

3. The method according to claim 1 wherein the dipeptide is a β-alanyl dipeptide.

4. The method according to claim 1 wherein the dipeptide is selected from the group consisting of carnosine, anserine and β-alanylglycine.

5. The method according to claim 1 wherein the sugar-dipeptide conjugate is a food ingredient.

6. The method according to claim 1 wherein the liquid eutectic mixture is formed by first dissolving the at least two compounds solid at 25° C. in an amount of water sufficient to dissolve all the compounds solid at 25° C. individually, and then concentrating the resulting solution until the water is present in an amount insufficient to dissolve all the compounds solid at 25° C. individually.

7. The method according to claim 1 wherein the dipeptide and the reducing sugar are present in a molar ratio between 1:0.02 and 1:50.

8. The method according to claim 1 wherein the liquid eutectic mixture comprises glucose, sucrose, carnosine and water.

9. The method according to claim 1 wherein the liquid eutectic mixture comprises glucose, carnosine and water.

10. The method according to claim 1 wherein the liquid eutectic mixture comprises glucose, and the molar ratio of glucose to water in the liquid eutectic mixture is between 1:9.5 and 1:2.5.

11. Method A method for preparing a food product comprising: forming a liquid eutectic mixture of at least two compounds solid at 25° C. and water, the water being present in an amount insufficient to dissolve all the compounds solid at 25° C. individually, or in an amount such that all the compounds solid at 25° C. are simultaneously saturated at 25° C.; and heating the liquid eutectic mixture at a temperature greater than 30° C. for at least 10 minutes to form a sugar-dipeptide conjugate; wherein the liquid eutectic mixture comprises a dipeptide and a reducing sugar; and combining the sugar dipeptide conjugate with food components to form a food product.

12. The method according to claim 11 wherein the food product is selected from the group consisting of a culinary seasoning, a cooking aid, a sauce, a soup and a pet-food product.

* * * * *